United States Patent [19]
Marks et al.

[11] Patent Number: 4,668,773
[45] Date of Patent: May 26, 1987

[54] ORGANOLANTHANIDE CATALYSTS

[75] Inventors: Tobin J. Marks; Heiko Mauermann, both of Evanston, Ill.

[73] Assignee: Northwestern University, Evanston, Ill.

[21] Appl. No.: 715,927

[22] Filed: Mar. 25, 1985

[51] Int. Cl.$^4$ .......................... C07F 7/02; B01J 21/06; B01J 31/12
[52] U.S. Cl. ........................................ 534/15; 556/11; 502/263; 502/302; 502/303; 502/304; 502/152
[58] Field of Search ................... 534/15; 502/263, 302, 502/303, 304, 152; 556/11

[56] References Cited

U.S. PATENT DOCUMENTS

| Re. 29,368 | 8/1977 | Pez | 534/15 X |
| 2,831,880 | 4/1958 | Benkeser | 556/11 |
| 3,060,215 | 10/1962 | Rosenberg et al. | 556/11 |
| 3,849,459 | 11/1974 | Maitlis et al. | 502/152 X |
| 3,969,386 | 7/1976 | Ballard et al. | 534/15 X |

OTHER PUBLICATIONS

Evans et al, *Organolanthanide Hydride Chemistry, 3. Reactivity of Low-Valent Samarium with Unsaturated Hydrocarbons Leading to a Structurally Characterized Samarium Hydride Complex,* JACS 1983, 105, 1401–1403.
Watson et al, *Homogeneous Lanthanide Complexes as Polymerization and Oligomerization Catalysts: Mechanistic Studies,* ACS Symposium Series, 1983, 212, 459–479.
Watson and Parshall, *Organolanthanides in Catalysis,* Acc. Chem. Res 1985, 18, 51–56.
Mauermann, Swepston and Marks, *$5f^3$ vs. $4f^3$, Routes to and Properties of Highly Reactive Neodymium (III) Hydrocarbyl and Hydride Complexes,* Organometallics, 4, 200, (1985).

*Primary Examiner*—John F. Terapane
*Assistant Examiner*—Susan Wolffe
*Attorney, Agent, or Firm*—Welsh & Katz, Ltd.

[57] ABSTRACT

The reaction of the organolanthanide complexes $[\eta^5-(CH_3)_5C_5]_2MCl_2^-Li((C_2H_5)_2O)_2^+$, M=La, Nd, Sm, Lu, with $LiCH[Si(CH_3)_3]_2$ provides a straight-forward route to ether-free and halide-free bis(pentamethylcyclopentadienyl) lanthanide alkyls, $(\eta^5(CH_3)_5C_5)_2MCH-[Si(CH_3)_3]_2$. The $(\eta^5(CH_3)_5C_5)_2NdCH[Si(CH_3)_3]_2$ complexes react with $H_2$ under mild conditions to yield the corresponding hydrides $[(\eta^5(CH_3)_5C_5)_2MH]_2$. These complexes have been found to be extremely active homogeneous olefin polymerization catalysts, as well as catalysts for olefin and acetylene hydrogenation.

6 Claims, No Drawings

ORGANOLANTHANIDE CATALYSTS

This application relates to catalysts and more particularly to a method for synthesizing organolanthanide catalysts, the catalysts themselves, and methods for use of such catalysts.

BACKGROUND OF THE INVENTION

Much of the recent development of early transition and f-element hydrocarbyl and hydride chemistry can be attributed to the beneficial characteristics of bis(pentamethylcyclopentadienyl), $[\eta^5(CH_3)_5C_5]_2$ (hereinafter) $Cp_2'$) supporting ligation. However, in studies of isoelectronic, isoleptic 4f/5f systems, it appears that synthesis routes to lanthanide $Cp_2'MR$ and $(Cp_2'MH)_2$ complexes were circuitous for late lanthanides and unknown for early (La-Nd) lanthanides. The latter appear of greatest interest since U(III)[6] and Nd(III)[5] are isoelectronic, because the early organolanthanides have the greatest importance in catalysis, and because, a priori, the early lanthanides might, for a given ligand array, offer the greatest degree of coordinative unsaturation and possibly reactivity. In addition, the early lanthanides are easily available and inexpensive. In planning syntheses, the use of highly lipophilic, sterically bulky R functionalities was anticipated so that undesirable coordination to the lanthanide ion of ether or halide ligands (normally present during the preparation of $Cp_2'MR$ complexes) could be avoided. In most d-element hydrocarbyl syntheses, the choice of R is also frequently dictated by the desire to avoid destabilizing β-hydrogen atoms. However, it now appears that β-alkyl elimination (e.g. eq. (1)) may be an equally important

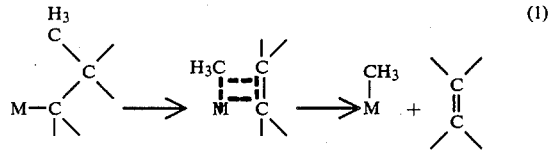

(1)

decomposition pathway for some organo-f-element complexes and must also be considered in ligand selection.

Bulky ligands such as $CH[Si(CH_3)_3]_2$, hereinafter (CHTMS2), offer both the attraction of substantial lipophilic bulk, a lack of β-hydrogen atoms, as well as a defense (heretofore largely unappreciated) against β-alkyl elimination since such an elimination process would produce a relatively high energy Si=C bond (e.g., eq. (2)). In the present invention, this ligand is

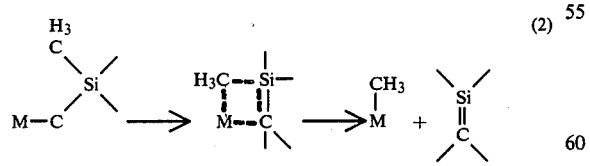

(2)

employed to straight-forwardly synthesize a broad class of stable $Cp_2'MR$ complexes ranging from the lightest (M=La) to the heaviest (M=Lu) lanthanide. Other bulky ligands such as the mesitylene ligand afford similar properties. With both ligands, hydrogenolysis is shown to readily yield the corresponding series of hydride dimers, $(Cp_2'MH)_2$ for M=La to Lu. The rather extraordinary reactivity of these molecules is demonstrated herein by their very high activity in olefin oligomerization and polymerization. Also shown is the surprisingly high activity of the catalysts of the subject invention for olefin hydrogenation.

Mechanistically, homogeneous olefin hydrogenation catalysis with early transition metal, lanthanide, and actinide catalysts is not well understood, and offers a much different mechanistic situation than conventional Group VIII or late transition element catalysts. In particular, the metal center may be in a relatively high ($\geq 3$) formal oxidation state, and/or it may not possess energetically accessible formal oxidation states for oxidative addition/reductive elimination processes, and/or it may be engaged in relatively polar metal-ligand bonding with a strong preference for "hard" ligands (not olefins), and may exhibit unusual M-H/M-C bond disruption enthalpy relationships vis-a-vis middle and late transition elements. Lanthanide ions represent the extreme cases of many of the above considerations, and as such can offer an opportunity to better understand hydrogenation catalysis in such environments.

SUMMARY OF THE INVENTION

Therefore, an object of the subject invention is the synthesis of lanthanide catalysts for use in polymerization and hydrogenation reactions.

Another object of the subject invention is a shelf-stable environmentally acceptable lanthanide catalyst and an intermediate for generating a lanthanide catalyst for use in a method for the polymerization of α-olefins and cycloalkenes.

A further object of the subject invention is a shelf stable and environmentally acceptable lanthanide catalyst and an intermediate for generating such a lanthanide catalyst for use in a method for the hydrogenation of olefins.

These and other objects are attained in accordance with the present invention wherein the reaction of $(\eta^5-(CH_3)_5C_5)_2MCl_2^-Li((C_2H_5)_2O)_2^+$ with $LiCH[Si(CH_3)_3]_2$, yields the early lanthanide alkyl $(\eta^5-(CH_3)_5C_5)_2MCH[Si(CH_3)_3]_2$, (hereinafter $Cp_2'MCHTMS2$) and the reaction of $(\eta^5-(CH_3)_5C_5)_2MCl_2^-Li((C_2H_5)_2O)_2^+$ with 2-lithium-mesitylene to yield the early lanthanide aryl 2-$[(\eta^5(CH_3)_5C_5)_2M]$-mesitylene; where M=a Lanthanide Series element, i.e., La, Ce, Pr, Nd, Pm, Sm, Ea, Gd, Tb, Dy, Ho, Er, Tm, Yb and Lu. Such lanthanide alkyl complexes may simplistically be drawn as:

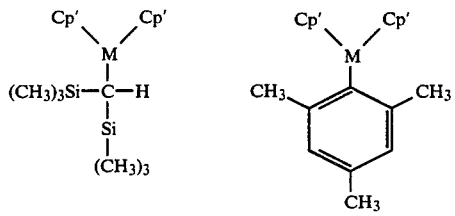

These ether- and halide-free bis(pentamethylcyclopentadienyl)lanthanide alkyls and aryls are relatively stable intermediates which may then be stirred under a hydrogen atmosphere, to form $[(\eta^5(CH_3)_5C_5)_2MH]_2$ (hereinafter $(Cp_2'MH)_2$, (where M=a Lanthanide Series element as set forth above) which has been found to be an efficient and highly active catalyst for use in olefin and cycloalkene polymerization, and olefin and acetylene hydrogenation. These lanthanide alkyls have the beneficial properties of having low toxicity and being otherwise environmentally unobjectionable.

DETAILED DESCRIPTION OF THE INVENTION

Materials and Methods

All operations were performed with rigorous exclusion of oxygen and moisture in flamed Schlenk-type glassware in a dual manifold Schlenk line or interfaced to a high vacuum ($10^{-5}$ torr) system, or in a nitrogen filled glovebox with a high capacity atmosphere recirculator. Argon, ethylene, propylene, dihydrogen, and deuterium gas were purified by passage through a supported MnO oxygen removal column and a molecular sieve column. Aliphatic hydrocarbon solvents were pretreated with conc. $H_2SO_4$, $KMnO_4$ solution, $MgSO_4$, and Na+4A molecular sieves. All reaction solvents were distilled from Na/K/benzophenone under nitrogen and were condensed and stored in vacuo in bulbs on the vacuum line containing a small amount of $[Ti(\eta^5-C_5H_5)_2Cl]_2ZnCl_2$ as indicator. Cyclohexane and heptane were additionally vacuum transferred onto Na/K and stirred for at least a day before use in catalytic experiments. The olefins, all hexenes, and cyclohexene were purified by stirring over Na/K for at least 6 hours and were freshly vacuum transferred. Deuterated solvents were dried over Na/K alloy and vacuum transferred before use.

Anhydrous lanthanide halides were prepared from the corresponding oxide and ammonium chloride. Pentamethylcyclopentadiene was prepared by the procedure set forth in Organometallics, 1984, 3, 819–821. The complexes $Cp_2'NdCl_2-Li((C_2H_5)_2O)_2^+$ and $Cp_2'LuCl_2-Li((C_2H_5)_2O)_2^+$ were prepared as known in the art. Bis(trimethylsilyl)methyllithium (LiCHTMS$_2$) and 2-lithium-mesitylene were also prepared as known in the art.

Catalyst Syntheses

In general, Cp$_2$'MCHTMS$_2$ and 2-(Cp$_2$'M)mesitylene may be prepared by mixing approximately equimolar amounts of $Cp_2'MCl_2Li(C_2H_5)_2O)_2'$ and LiCHTMS$_2$ or 2-lithium-mesitylene, as appropriate, in toluene for 8–16 hours (preferably 12 hours) and −10° C. to 25° C. (preferably 0° C.). The solvent is then removed and the residue extracted with another solvent, preferably pentane. The extract is cooled to recrystallize the Cp$_2$'MCHTMS$_2$ or 2-(Cp$_2$'M)mesitylene.

EXAMPLE 1

$Cp_2'LaCl_2-Li((C_2H_5)_2O)_2^+$

A suspension of 2.1 g (8.6 mmol) anhydrous LaCl$_3$ and 2.44 g (17.2 mmol) LiCp' in 120 ml THF was refluxed for 12 hours at 0° C. The solvent was then removed in vacuo, being careful to keep the temperature below 10° C. to avoid formation of a less reactive complex (probably (Cp$_2$'LaCl)$_2$). The white residue was then extracted with 200 mL diethyl ether, the mixture filtered, reduced in volume to 30 mL, and slowly cooled to −30° C. Decantation of the solvent and drying under high vacuum yielded 2.7 g (49.4%) of $Cp_2'LaCl_2-Li((C_2H_5)_2O)_2^+$ as a white, microcrystalline solid. Additional product can be obtained from the mother liquor.

EXAMPLE 2

Cp$_2$'LaCHTMS$_2$

A suspension of 2.6 g (4.11 mmol) $Cp_2'LaCl_2-Li((C_2H_5)_2)_2^+$ and 0.68 g (4.1 mmol) LiCHTMS$_2$ in 150 mL toluene was stirred for 12 hours at 0° C. The solvent was then removed in vacuo and the white residue extracted with 100 mL pentane. The resulting mixture was then filtered, the volume of the filtrate reduced to 30 mL, and the filtrate slowly cooled to −30° C. Pale yellow crystals of Cp$_2$'LaCHTMS$_2$ were isolated by decantation and subsequent vacuum drying. Yield: 1.4 g (60%).

EXAMPLE 3

Cp$_2$'NdCHTMS$_2$

The above procedure set forth in Examples 1 and 2 was repeated with 5.1 g (8.0 mmol) $Cp_2'NdCl_2-Li((C_2H_5)_2O)_2^+$ and 1.32 g (8.0 mmol) LiCHTMS$_2$ in 50 mL toluene to yield, after work-up and recrystallization from pentane, 3.67 g (80%) of Cp$_2$'NdCHTMS$_2$ as blue-green crystals.

EXAMPLE 4

Cp$_2$'SmCHTMS$_2$ (One-pot procedure)

A mixture of 1.00 g (3.90 mmol) SmCl$_3$ and 1.11 g (7.79 mmol) LiCp' was refluxed in 50 mL THF for 8 hours at 0° C. The solvent was then removed in vacuo and the residue, together with 0.65 g (3.94 mmol) LiCHTMS$_2$, was suspended in 50 mL toluene at −78° C. The mixture was allowed to gradually warm to room temperature over the next 12 hours, the solvent removed under high vacuum, and the residue extracted with 50 mL pentane. Subsequent filtration, slow cooling of the filtrate to −78° C., filtration and drying produced 0.600 g (27%) of Cp$_2$'SmCHTMS$_2$ as red-brown crystals. An additional 0.400 g (18%) of product can be recovered from the mother liquor (total yield=45%).

EXAMPLE 5

Cp$_2$'LuCHTMS$_2$

The aforementioned procedure set forth in Example 4 for Cp$_2$'LaCHTMS$_2$ was carried out with 3.1 g (4.62 mmol) $Cp_2'LuCl_2-Li((C_2H_5)_2O)_2^+$ and 0.79 g (4.7 mmol) LiCHTMS$_2$ in 150 mL of toluene. The standard workup and pentane recrystallization yielded 1.8 g (64%) of Cp$_2$'LuCHTMS$_2$ as colorless crystals.

(Cp$_2$'MH)$_2$ compounds may be prepared by stirring Cp$_2$'MCHTMS$_2$/pentane or 2-(Cp$_2$'M)mesitylene/pentane under a hydrogen atmosphere for 0.1–1.5 hours (preferably 2 hours) at a temperature of −10° C. to 10° C. (preferably 0° C. ). The resulting precipitate may be isolated by filtration, washing and the like.

EXAMPLE 6

(Cp$_2$'LaH)$_2$

Cp$_2$'LaCHTMS$_2$ (0.200 g, 0.35 mmol) was stirred under and H$_2$ atmosphere in 50 mL of pentane for 2 hours at 0° C. The resulting colorless precipitate was isolated by filtration, washed with 2×3 mL pentane, and dried in vacuo to yield 0.14 g (98%) (Cp$_2$'LaH)$_2$ as a colorless, microcrystalline solid.

EXAMPLE 7

$(Cp_2'NdH)_2$

The above procedure set forth in Example 6 was carried out with 1.00 g (1.74 mmol) $Cp_2'NdCHTMS_2$ in 50 mL pentane. Filtration, washing, and drying yielded 0.600 g (83%) of $(Cp_2'NdH)_2$ as a blue-green, microcrystalline powder.

EXAMPLE 8

$(Cp_2'SmH)_2$

This compound was prepared from $Cp_2'SmCHTMS_2$ using the procedure above for $(Cp_2'LaH)_2$ set forth in Example 6 and was isolated as a pink powder.

EXAMPLES 9

$(Cp_2'LuH)_2$

This complex was prepared by the aforementioned procedure for $(Cp_2'LaH)_2$ as set forth in Example 6 using $H_2$ in pentane. The yield of $(Cp_2'LuH)_2$ was 98% colorless, polycrystalline solid.

EXAMPLE 10

$Cp_2'Nd(\eta^3-C_3H_5)$

A solution of $Cp_2'NdCHTMS_2$ (1.00 g, 1.74 mmol) in 50 mL pentane was stirred overnight under an $H_2$ atmosphere at 0° C. The resulting precipitate of $(Cp_2'NdH)_2$ was filtered off and washed well with cold pentane. The hydride was then suspended in 50 mL pentane at −78° C., and with stirring, a 3-4 molar excess of propylene was introduced. The suspension was slowly warmed to −15° C. and then stirred for 3.5 hours at this temperature (dissolution of the hydride was visible by −30° C.). At this time, all of the hydride had reacted (as evidenced by dissolution), and the excess propylene and pentane were removed in vacuo. The residue was then redissolved in 30 mL of pentane and slowly cooled overnight to −78° C. The resulting large green-brown crystals were filtered off and washed with cold pentane to yield 0.49 g (62%) of $Cp_2'Nd(\eta^3-C_3H_5)$.

Olefin Polymerization

α-olefins, such as ethylene, propylene, 1-hexene and butadiene, and cycloalkenes, such as cyclohexene, were polymerized in a 500 mL flamed round bottom reaction flask attached to a high vacuum line. The flask was fitted with Morton-type indentations, and an overhead mechanical stirrer (high speed stirring motor, large Teflon ® paddle). The shaft of the stirrer could be sealed to allow high vacuum pump down. The flask was also equipped with two straight-bore high vacuum stopcocks. In a typical polymerization procedure, the exterior connecting tube of one stopcock (ca. 10 mm in length) was sealed with a new serum cap. The reaction vessel was then pumped down for several hours, backfilled with inert gas, the stopcock closed, the flask re-evacuated, and a measured quantity of solvent (cyclohexane or heptane) vacuum transferred into the reaction flask from Na/K. Next, gaseous ethylene or propylene was admitted to the vessel through the gas purification column. The gas pressure was continuously maintained at approximately 1.0 atm with a mercury manometer apparatus and the temperature maintained at approximately −78° C. to +80° C. Rapid stirring of the solution was initiated, and after several minutes (to allow saturation of the solvent with olefin), the stopcock was opened and a small aliquot of approximately 5.0 mM catalyst solution of Cp'MR or (Cp'MH)$_2$ (where M=La, Nd or Sm) in cyclohexane was injected by gas-tight syringe just above the rapidly stirring solution (the syringe needle had been flattened so that the catalyst solution exited in a fine spray). In the case of ethylene, voluminous quantities of polyethylene generally formed within seconds. After a measured time interval, the polymerization was then quenched by injecting methanol through the serum cap of the second stopcock. The polymeric product was collected by filtration, washed with methanol, and dried under high vacuum. Identical results were obtained using toluene as the reaction solvent.

For 1-hexene/ethylene copolymerizations, ethylene gas was admitted at various pressures to a stirring solution of the catalyst in with another appropriate α-olefin, such as 1-hexene or 1-butene. Quenching of the polymerization and product isolation were as described for polyethylene.

Olefin Dimerization

EXAMPLE 11

Reactions with 1-Hexene

Using high vacuum techniques, approximately 0.25 mmol of $(Cp_2'NdH)_2$ or $(Cp_2'LaH)_2$ was reacted with an approximately 10-fold excess of 1-hexene in 10 mL of pentane. The reaction was begun at approximately −78° C. and was brought to approximately −10° C. over a period of 2-3 hours. After several additional hours at −10° C., the hydride had dissolved. The solvent and other volatiles were then removed under high vacuum and the residue dissolved in cyclohexane. The resulting solution was filtered.

The 1-hexene dimer was prepared by slowly stirring 50 mg of the appropriate $(Cp_2'MH)_2$ complex with 3.0 mL of 1-hexene under 1 atm of $H_2$ for 1 hour. After this time, hexane was removed in vacuo at room temperature and the remaining liquid was vacuum transferred using a heat gun. GC/MS showed it to comprise about 99% $C_{12}H_{26}$ with about 1% higher oligomers. The total yield of oligomers was approximately 10%.

EXAMPLE 12

Reaction with Butadiene

Using the same procedure as in Example 11 for 1-hexene above, $(Cp_2'LaH)_2$ was reacted with an approximately 10-fold excess of butadiene in pentane, and the product taken up in cyclohexane.

EXAMPLE 13

Reactions with Cyclohexene

Using the procedure described above in Example 11 for 1-hexene, cyclohexene was reacted with $(Cp_2'NdH)_2$ and $(Cp_2'LaH)_2$.

All of the above polymerization and dimerization chemistry was carried out under rigorously anaerobic, moisture-free, high vacuum line conditions. At room temperature and one atmosphere ethylene pressure, the $Cp_2'MCHTMS_2$ complexes (M=La, Nd, and Sm) failed to react with ethylene over the course of several hours. Although the absence of migratory insertion may be explained on steric grounds, it should be noted that the same complexes undergo rapid M-CHTMS$_2$ bond hydrogenolysis and migratory CO insertion. In contrast to the $Cp_2'MCHTMS_2$ complexes, the corresponding $(Cp_2'MH)_2$ complexes undergo extremely rapid reaction with ethylene at room temperature to produce voluminous quantities of polyethylene within seconds of contacting the two reagents.

Data pertaining to the polymerization experiments are set out in Table I. A number of points are noteworthy. First, it is evident that chain propagation is extremely rapid. The order of reactivity follows decreasing ionic radius: La>Nd>Lu. Furthermore, the early lanthanide systems display maximum activities comparable to or in excess of those reported for the most active "homogeneous" ethylene polymerization catalysts currently known as well as those for most heterogeneous organometallic molecule/inorganic support systems. Indeed, $(Cp_2'MH)_2$ activities appear to approach those of heterogeneous "third generation" Ziegler-Natta catalysts. These organolanthanide hydride compounds also exhibit measurable activity even at $-78°$ C. The $(Cp_2'MH)_2$/ethylene turnover frequencies and catalyst efficiencies were estimated by quenching the polymerization reaction after measured time intervals and weighing the quantity of polyethylene produced. As such, these estimates are clearly lower limits to the reactivities of the most active catalysts and evidence for both reactor and microscopic mass transport effects is clear from the entries in Table I. Thus, when identical reaction procedures are carried out with increasing quantities of catalyst at identical overall concentrations, the apparent turnover frequency and catalyst efficiency falls, implicating inadequate monomer delivery to the reacting species (and showing that "poisoning" effects of residual air, water, impurities, etc. may not be significant, i.e., very little of the catalyst serves a sacrificial role). For the less active $(Cp_2'LuH)_2$ catalyst, the turnover frequency is relatively insensitive to catalyst concentration, quantity and reaction times (Table I).

Besides the obvious effect of stirring inefficiency, the heterogenous nature of the reaction environment due to the precipitation of polyethylene as the reaction proceeds is no doubt a contributor to microscopic mass transport effects. That the most active La and Nd catalysts exhibit a general pattern of falling turnover frequency and catalyst efficiency with increasing reaction time (entries 1 and 2; 5 and 6) suggests that diffusion of ethylene to the entrained catalytic centers becomes increasingly difficult as solid polymer accumulates. The general pattern of decreasing efficiency with increasing catalyst concentration are also possibly mass transport related. Hydride dimer dissociation equilibria (which should scale as $[M]^{\frac{1}{2}}$) should only affect the initiation rate (rather than propagation). Although no quantitative information on the relationship of these rates is available, the molecular weight distribution data and the observation that unhindered olefins react extremely rapidly with the hydrides argue that initiation rates must be comparable to or greater than those for propagation. In regard to heating effects, the dilute conditions and short reaction times do not result in significant changes in the temperature of the bulk reaction mixtures. It is, however, more difficult to rule out the importance of "local," heterogeneity-related effects, although it is not readily apparent how modest local heating would diminish turnover frequencies.

For a completely homogeneous, kinetically well-behaved (propagation as described by $k_p$ remains constant throughout the polymerization), irreversible polymerization in which termination (described by $k_t$), chain transfer (described by $k_{ct}$), and poisoning are insignificant and in which initiation is instantaneous, a Poisson molecular weight distribution is expected for high degrees of polymerization. That is, the polymer (a "living polymer") should be virtually monodisperse, i.e., $M_w/M_n = 1.0$. Under similar constraints but admitting the operability of termination and chain transfer (and assuming $k_p$, $k_t$, and $k_{ct}$ remain constant throughout the polymerization) the "most probable" molecular weight distribution is expected, i.e., $M_w/M_n = 2.0$. We suspect that the living polymer regime is operative for the present systems, modified principally by possible mass transport and heterogeneity effects. In regard to irreversibility, the polymerization is far from thermoneutral ($\Delta H \simeq -26$ kcal/mol) and, with reference to termination/chain transfer processes, thermochemical data and experiments with 1-hexene argue that $\beta$-hydride elimination (eq. (3)) should be:

$$MCH_2CH_2P \rightleftharpoons MH + CH_2 = CHP \quad (3)$$

TABLE I

Ethylene Polymerization by $(Cp_2MH)_2$ Compounds[a]

| Entry | Compound M = | Concentration μM | Temperature °C. | Time s | $N_t$ s$^{-1}$ | Efficiency g/mmol min atm | $\overline{M}_n \times 10^{-3}$ | $\overline{M}_w \times 10^{-3}$ | $\overline{M}_z \times 10^{-3}$ | $\overline{M}_w/\overline{M}_n$ | Chains/M |
|---|---|---|---|---|---|---|---|---|---|---|---|
| 1. | La | 26 | 25 | 5 | 1450 | 2440 | 428 | 843 | 1,405 | 1.97 | 0.43 |
| 2. | La | 27 | 25 | 10 | 690 | 1160 | 227 | 1,463 | 5,077 | 6.42 | 0.85 |
| 3. | La | 13 | 25 | 5 | 1800 | 3040 | 676 | 1,371 | 2,552 | 2.03 | 0.37 |
| 4. | Nd | 11 | 25 | 10 | 1120 | 1888 | — | — | — | — | — |
| 5. | Nd | 22 | 25 | 10 | 640 | 1080 | — | — | — | — | — |
| 6. | Nd | 22 | 25 | 5 | 1360 | 2280 | 590 | 1,070 | 1,649 | 1.81 | 0.32 |
| 7. | Nd | 60 | 25 | 10 | 380 | 640 | 233 | 1,034 | 2,450 | 4.46 | 0.46 |
| 8. | Nd | 60[b] | 25 | 10 | 420 | 705 | | | | | |
| 9. | Nd | 60[b] | 25 | 30 | 337 | 567 | | | | | |
| 10. | Nd | 60[b] | 25 | ·60 | 230 | 386 | | | | | |
| 11. | Nd | 60[b] | 25 | 180 | 82 | 138 | | | | | |
| 12. | Nd | 60[b] | 32 | 30 | 280 | 470 | | | | | |
| 13. | Nd | 27[c] | 54 | 10 | 619 | 1040 | | | | | |
| 14. | Nd | 133[b] | 25 | 10 | 479 | 835 | | | | | |
| 15. | Nd | 22 | −78 | 600 | 5.2 | 8.7 | 648 | 1,264 | 2,589 | 1.95 | 0.13 |
| 16. | Lu | 25 | 25 | 45 | 97 | 162 | 250 | 377 | 472 | 1.50 | 0.49 |
| 17. | Lu | 13 | 25 | 60 | 95 | 157 | 361 | 605 | 817 | 1.68 | 0.44 |
| 18. | Lu | 140 | 25 | 20 | 100 | 167 | 96 | 132 | 151 | 1.37 | 0.58 |

[a]All reactions carried out in 140 ml. cyclohexane except where indicated.
[b]Carried out in 40 ml. cyclohexane.
[c]Carried out in 88 ml. cyclohexane Such an elimination would be quite endothermic for a straight-chain primary alkyl. The operability of other termination (e.g., Cp'H atom abstraction), chain transfer or impurity-related processes is more difficult to assess.

Copolymerizations

As known in the art, the Cp$_2$'M coordination sphere is apparently too constricted to support the rapid polymerization of olefins bulkier than ethylene (few homogeneous catalysts are known to be effective). However, we have found that α-olefins, such as 1-hexene, propylene, butadiene, 1-butene and the like, can be copolymerized with ethylene by stirring solutions of (Cp$_2$'MH)$_2$, such as (Cp$_2$'NdH)$_2$ under an ethylene atmosphere at various pressures. This process presumably involves ethylene at the insertion step. It was also found that Cp$_2$'Nd($\eta^3$-allyl) was effective in initiating ethylene polymerization. Such a process is likely to involve the monohapto form of the allyl (eq. (4)).

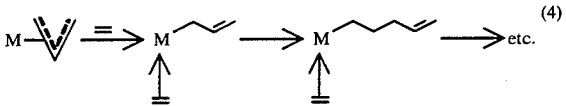

(4)

Olefin Hydrogenation

Rapidly stirring any of the (Cp$_2$'MH)$_2$ complexes with 1-hexene under 1 atm of H$_2$ reveals that they are extremely active hydrogenation catalysts (N$_t$ values are as high as 120,000/hour). The mechanistic details of the catalytic hydrogenation chemistry are, briefly stated: (i) addition of metal hydride to olefin to produce a hexyl complex and (ii) hydrogenolysis of the metal-carbon bond to yield alkane (hexane) and to regenerate the metal hydride.

All of the following examples were performed under rigorously anhydrous and anaerobic conditions employing the procedures, methods, and precautions described previously. Solvents were purified and distilled as set forth above, were stored (with stirring) over Na/K, and were vacuum transferred from Na/K immediately prior to use. The olefins 1-hexene, cyclohexene, trans-2-hexene, trans-3-hexene, and cis-2-hexene were dried by stirring over Na/K for at least 6 hours and were freshly vacuum transferred. The acetylene 3-hexyne was dried by repeated vacuum transfer onto freshly activated molecular sieves followed by vacuum transfer onto Na/K, stirring for about 1 hour, vacuum transferring, and repeated freeze-thaw degassing. Purity of the final fraction was verified by GC. Hydrogen, argon, and deuterium were purified by passing sequentially through regularly activated MnO, and 4A molecular sieve columns. Organolanthanide complexes were prepared as set forth above.

EXAMPLE 14

An oven-dried reaction vessel equipped with three burettes for the catalyst solution, the solvent, and the olefin, respectively, was attached to the vacuum line while still hot, pumped down for at least 1 hour, closed under vacuum, and taken into a glove box with a high capacity recirculating system. The burettes were then filled with a solution of (Cp$_2$'MH)$_2$ or (Cp$_2$'MR) (freshly prepared on the vacuum line using calibrated volumetric vessels) and 1-hexene. The reaction vessel was then filled with a measured quantity of freshly distilled toluene, closed, and transferred outside to the vacuum line. The reaction volume was evacuated and the solvent freeze-thaw degassed, back-filling repeatedly with H$_2$. Next, the thermostatted water circulating system was connected and actuated. After all parts of the system had been given appropriate time to reach thermal equilibrium and equilibrium with the reactor atmosphere, measured volumes of catalyst solution and olefin were added to the reaction vessel. High speed vortex mixing was then initiated and the H$_2$ pressure recorded as a function of time. Appropriate corrections in data analysis were made for solvent and reactant/product vapor pressures. In general, conditions were adjusted such that all of the olefin was consumed in 0.13–10 minutes and the overall pressure drop in the system was always less than 2% (usually less than 1%). The hydrogenation of 1-hexene in the above manner by the members of the organolanthanide catalysts of the subject invention was found to be extremely rapid. In both series, the relative ordering of activities was found to be approximately inversely proportional to metal ionic radius: Lu > Sm > Nd > La.

EXAMPLE 15

Cyclohexene was hydrogenated using the procedure of Example 14 with (Cp$_2$'MH$_2$)$_2$ solution used as catalyst for M=La, Nd, Sm and Lu.

In general the trends in activity observed for cyclohexene hydrogenation parallel ionic radius, i.e., La > Nd > Sm > Lu (excepting anomalous (Cp$_2$'LuH)$_2$). This is opposite the trend for 1-hexene hydrogenation.

EXAMPLE 16

3-hexyne was hydrogenated according to the procedure of Example 14, utilizing (Cp$_2$'MH)$_2$ with M=La, Nd, Sm and Lu. As monitored manometrically and by GC/MS, the hydrogenation for all M elements proceeds slowly (relatively) until essentially all of the 3-hexyne is converted to cis-3-hexene (eq. (5)) at which point the rate of gas uptake accelerates by a factor of about 10.

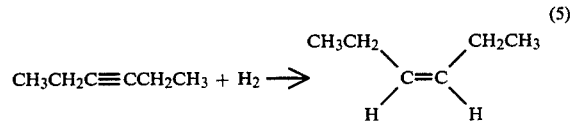

(5)

The relative rates for the first stage are Lu > Sm > Nd > La.

The second stage of 3-hexyne reduction, conversion of cis-3-hexene to n-hexane, is considerably more rapid than the first. Although approximate rate data could be extracted from the hexyne→hexene→hexane data, kinetic orderings were more conveniently and accurately determined from independent experiments with cis-3-hexene.

EXAMPLE 17

Hydrogenation of Other Hexenes

Other hydrogenation reactions were also carried out with trans-2-hexene, trans-3-hexene, and cis-2-hexene using (Cp$_2$'MH)$_2$ catalysts according to the procedure of Example 14. For trans-2-hexene, the activity trend Lu > Sm > Nd > La parallels that observed for 1-hexene. In these reactions, it was observed that the relative activities trans-3-hexene > 1-hexene > trans-2-hexene are obeyed. For both Nd and Lu, the relative hydrogenation rates observed were cis-2-hexene>cis-3-hexene>cyclohexene.

are involved in the catalysts, but, rather a close coupling of olefin/hydride insertion (eq. (6))

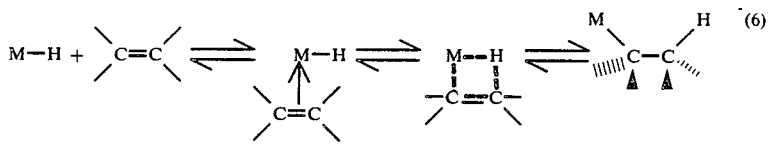

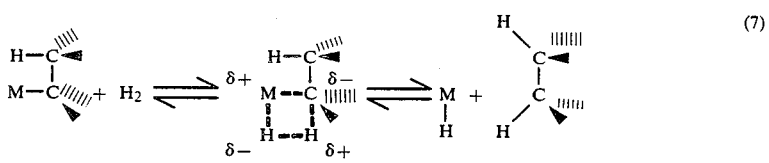

Hydrogenation of Other Olefins

Several exploratory experiments were conducted with other olefins. It was found that tetramethylethylene could not be hydrogenated by any of the present catalysts at a measurable rate (25° C., 1 at H$_2$ pressure). In a single experiment, neat r-(+) limonene was hydrogenated largely at the terminal C=C bond in 1.5 hours. Presumably the regio- and stereoselectivity of this type of reaction could be modified by varying the reaction time or conditions (e.g., H$_2$ pressure, addition of THF).

Heterogeneous Catalysis

In addition to the homogeneous catalytic processes described above, heterogeneous catalytic processes are envisioned as being within the scope of the subject invention as well. In such a heterogeneous process, the (Cp$_2$'MH)$_2$ would be adsorbed on the surface of a suitable inorganic substrate such as silica, silica gel, alumina, magnesium chloride, magnesium oxide or the like, and placed in contact with the reactants for polymerization or hydrogenation, as desired.

The synthetic chemistry presented here offers straightforward, general routes to a broad family of new ether-free, halide-free bis(pentamethylcyclopentadienyl)lanthanide alkyls and hydrides. The hydrides are of course greatly desirable synthetic targets for catalytic studies, but are equally valuable precursors for numerous types of ether-free, halide-free lanthanide hydrocarbyls and other derivatives. One result of this work is thus a readily accessible, homologous series of tractable, thermally stable, very electrophilic and very highly reactive lanthanide alkyl/hydride pairs which span the 4f block from the lightest (4f$^0$) to heaviest member (4f$^{14}$). In chemistry involving olefins, significant reactivity differences are observed between light (La, Nd) and heavy (Lu) lanthanides. For example, the light members appear to be the most active homogeneous ethylene polymerization catalysts prepared to date.

By the hydrogenation examples set forth above, it can be seen that the organolanthanide (Cp$_2$'MH)$_2$ appears to be one of the more active homogeneous olefin hydrogenation catalysts yet discovered. There is no evidence that oxidative addition/reductive elimination sequences are involved in the catalysts, but, rather a close coupling of olefin/hydride insertion (eq. (6)) followed by "four-center" hydrogenolysis (eq. (7)), drawn arbitrarily in an eclipsed conformation).

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the techings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

We claim:

1. An organolanthanide of the formula [$\eta^5$-(CH$_3$)$_5$C$_5$]$_2$MR where M is selected from the group consisting of the Lanthanide Series elements, and R is selected from the group consisting of mesitylene and CH(Si(CH$_3$)$_3$)$_2$.

2. A lanthanide alkyl of the formula [$\eta^5$-(CH$_3$)$_5$C$_5$]$_2$MCH[Si(CH$_3$)$_3$]$_2$ wherein M is selected from the group consisting of the Lanthanide Series elements.

3. The lanthanide alkyl of claim 2 wherein M is selected from the group consisting of La, Nd, Sm and Lu.

4. An organolanthanide of the formula [($\eta^5$(CH$_3$)$_5$C$_5$)$_2$MH]$_2$ where M is selected from the group consisting of La, Ce, Pr, Nd, Pm, Eu, Gd, Tb, Dy, Ho, Er and Tm.

5. A method for preparing (Cp$_2$'MH)$_2$ comprising the steps of contacting a lanthanide compound selected from the group consisting of Cp$_2$'MCH[Si(CH$_3$)$_3$]$_2$ and 2-(Cp$_2$'M)mesitylene, with H$_2$, wherein Cp'=$\eta^5$-(CH$_3$)$_5$C$_5$ and M is selected from the group consisting of the Lanthanide Series elements.

6. A method for the preparation of [$\eta^5$(CH$_3$)$_5$C$_5$]$_2$MCH[Si(CH$_3$)$_3$]$_2$ comprising the steps of mixing [$\eta^5$(CH$_3$)$_5$C$_5$]$_2$MCl$_2$—Li((C$_2$H$_5$)$_2$O)$_2$+ with approximately an equimolar amount of LiCH(Si(CH$_3$)$_3$)$_2$ in a solvent, and removing said solvent, wherein M is selected from the group consisting of the lanthanide elements.

* * * * *

UNITED STATES PATENT AND TRADEMARK OFFICE
CERTIFICATE OF CORRECTION

PATENT NO. : 4,668,773

DATED : May 26, 1987

INVENTOR(S) : Marks and Mauermann

It is certified that error appears in the above-identified patent and that said Letters Patent is hereby corrected as shown below:

Column 3, Line 46, change "$Cp_2' \ MCl_2Li \ (C_2H_5)_2O)_2'$" to --$Cp_2' \ MCl_2Li \ (C_2H_5)_2O)_2^+$--.

Column 4, Line 5-6, change "$Cp_2'LaCl_2^-Li \ ((C_2H_5)_2)_2^+$" to --$Cp_2'LaCl_2^-Li \ ((C_2H_5)_2 \ O)_2^+$--.

Table 1, change "$(Cp_2MH)_2$" to --$(Cp_2'MH)_2$--.

Column 12, Line 26, change "techings" to --teachings--.

Signed and Sealed this

Thirtieth Day of August, 1988

Attest:

DONALD J. QUIGG

*Attesting Officer*          *Commissioner of Patents and Trademarks*